(12) United States Patent
Emadzadeh

(10) Patent No.: US 10,456,053 B2
(45) Date of Patent: Oct. 29, 2019

(54) HEART RATE MONITOR

(71) Applicant: QuickLogic Corporation, Sunnyvale, CA (US)

(72) Inventor: Amir Abbas Emadzadeh, Campbell, CA (US)

(73) Assignee: QuickLogic Corporation, Sunnyvale, CA (US)

( * ) Notice: Subject to any disclaimer, the term of this patent is extended or adjusted under 35 U.S.C. 154(b) by 497 days.

(21) Appl. No.: 15/054,022

(22) Filed: Feb. 25, 2016

(65) Prior Publication Data

US 2017/0020398 A1    Jan. 26, 2017

Related U.S. Application Data

(60) Provisional application No. 62/195,730, filed on Jul. 22, 2015.

(51) Int. Cl.
*A61B 5/024* (2006.01)
*A61B 5/00* (2006.01)

(52) U.S. Cl.
CPC .......... *A61B 5/02438* (2013.01); *A61B 5/681* (2013.01); *A61B 5/7207* (2013.01); *A61B 5/6824* (2013.01); *A61B 5/7275* (2013.01); *A61B 5/7282* (2013.01)

(58) Field of Classification Search
CPC .......... A61B 5/7207; A61B 5/11; A61B 5/024
See application file for complete search history.

(56) References Cited

U.S. PATENT DOCUMENTS

| 8,180,591 B2 | 5/2012 | Yuen et al. |
| 8,920,332 B2 | 12/2014 | Hong et al. |
| 2003/0120164 A1* | 6/2003 | Nielsen ............... A61B 5/02055 600/513 |
| 2007/0051369 A1 | 3/2007 | Choi et al. |

(Continued)

OTHER PUBLICATIONS

Peng et al (Motion artifact removal from photoplethysmographic signals by combining temporally constrained independent component analysis and adaptive filter, 2014, BioMedical Engineering OnLine, 13(50): pp. 1-14).*

(Continued)

*Primary Examiner* — Patricia Mallari
*Assistant Examiner* — Tho Q Tran
(74) *Attorney, Agent, or Firm* — Silicon Valley Patent Group LLP

(57) ABSTRACT

A wrist worn heart rate monitor includes a photoplethysmogram (PPG) sensor and an inertial sensor. Signals from the inertial sensor are used to identify and remove noise from the PPG signals. An initial heart rate value is selected from a number of heart rate candidates that remain in the resulting PPG spectrum and is used to track the heart rate of the user. The PPG spectrum is monitored while tracking the heart rate to determine if the selected initial heart rate value is in error. The PPG spectrum may be monitored by determining a correlation of possible heart rate candidates in each PPG spectrum to the previous heart rate candidates and resetting the heart rate value accordingly. Additionally or alternatively, the PPG spectrum may be monitored by determining when only a single heart rate candidate is present in consecutive PPG spectra and resetting the heart rate value accordingly.

16 Claims, 6 Drawing Sheets

(56) References Cited

U.S. PATENT DOCUMENTS

| | | |
|---|---|---|
| 2007/0282176 A1 | 12/2007 | Shimada et al. |
| 2013/0053696 A1* | 2/2013 | Hasegawa-Johnson ............... A61B 8/02 600/453 |
| 2014/0213863 A1 | 7/2014 | Loseu et al. |
| 2014/0213920 A1 | 7/2014 | Lee et al. |
| 2016/0022220 A1* | 1/2016 | Lee ............ A61B 5/721 600/479 |
| 2016/0051157 A1* | 2/2016 | Waydo .......... A61B 5/02416 600/479 |
| 2017/0143218 A1* | 5/2017 | Pande .......... A61B 5/02416 |

OTHER PUBLICATIONS

Zahourian et al. (2008). "A spectral/temporal method for robust fundamental frequency tracking," *J. Acoust. Soc. Am.* 123(6):459-471.

Zhang (2015). "Photoplethysmography-Based Heart Rate Monitoring in Physical Activities via Joint Sparse Spectrum Reconstruction," IEEE Transactions on Biomedical Engineering: pp. 1-9.

Zhang et al. "TROIKA: A General Framework for Heart Rate Monitoring Using Wrist Type Photoplethysmographic Signals During Intensive Physical Exercise," IEEE Transactions on Biomedical Engineering, vol. 62, No. 2, pp. 522-531, Feb. 2015.

* cited by examiner

HEART RATE MONITOR

CROSS REFERENCE TO RELATED APPLICATIONS

This application claims priority under 35 USC 119 to U.S. Provisional Application No. 62/195,730, filed Jul. 22, 2015, which is incorporated by reference herein in its entirety.

FIELD OF THE INVENTION

The present invention relates to a heart rate monitor, and more specifically to a heart rate monitor that is worn on the user's wrist.

BACKGROUND

Heart rate monitors are used for measurement of a heart rate, e.g., for applications such as health monitoring, sports training, and fitness. Conventional devices capable of constantly monitoring a user's heart rate have been, until recently, cumbersome. For example, heart rate monitors often use electrocardiogram (EKG) signals, which require electrodes or a strap placed around the user's chest.

A less cumbersome technique for monitoring heart rate is based on pulse oximetry using a photoplethysmograph (PPG) sensor. A PPG sensor non-invasively measures the absorption of light passing through a user's tissue, e.g., a finger or an ear lobe, to determine the oxygen saturation level of arterial blood and heart rate. Arteries expand and contract due to blood flow and, thus, the amount of absorbed light changes in the course of a heart beat. The resulting signal is referred to as a photoplethysmograph (PPG). The PPG signal may be analyzed to determine, among other thing, the heart rate of the person to which the PPG sensor is attached.

Conventionally, pulse oximetry requires the user to remain relatively motionless to ensure that a good PPG signal is received. When a PPG sensor is used with a person that is in motion, artifacts in the PPG signal may be produced as a result of the user's motion as well as displacement of the PPG sensor. The resulting artifacts or noise result often result in inaccuracies in the estimated heart rate of the user.

SUMMARY

A wrist worn heart rate monitor includes a photoplethysmogram (PPG) sensor and an inertial sensor. Signals from the inertial sensor are used to identify and remove noise from the PPG signals. An initial heart rate value is selected from a number of heart rate candidates that remain in the resulting PPG spectrum and is used to track the heart rate of the user. The PPG spectrum is monitored while tracking the heart rate to determine if the selected initial heart rate value is in error, and if so, the heart rate value is reset. The PPG spectrum may be monitored by determining a correlation of possible heart rate candidates in each PPG spectrum to the previous heart rate candidates and resetting the heart rate value accordingly. Additionally or alternatively, the PPG spectrum may be monitored by determining when only a single heart rate candidate is present in consecutive PPG spectra and resetting the heart rate value accordingly.

DETAILED DESCRIPTION

Figure 1:
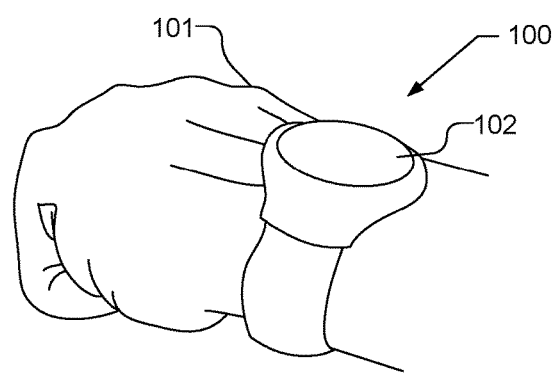
FIG. 1 illustrates a wrist worn heart rate monitor worn on the wrist of a user.
Figure 2:
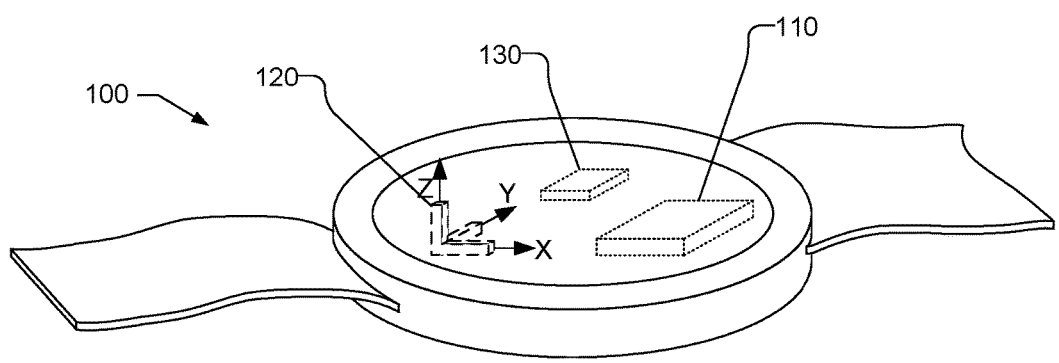
FIG. 2 schematically illustrates a wrist worn heart rate monitor.

FIG. 1 illustrates a wrist worn heart rate monitor 100 worn on the wrist of a user 101 and FIG. 2 schematically illustrates the wrist worn heart rate monitor 100. Portions of wrist bands are illustrated in FIG. 2 as extending from the sides of the heart rate monitor 100. The heart rate monitor 100 includes a PPG sensor 110, a multiple axis inertial sensor 120, and a processor 130. The processor 130 is coupled to receive the PPG signals from the PPG sensor 110 and the inertial sensor signals from the inertial sensor 120. The PPG sensor 110, the inertial sensor 120, and processor 130 are inside the heart rate monitor 100 and accordingly are illustrated with dotted lines. The processor 130 monitors the heart rate of the user 101 (shown in FIG. 1) based on the PPG signals and inertial sensor signals. The inertial sensor 120 may be, e.g., a 3 axis accelerometer, where the various axes are labeled X, Y, and Z in FIG. 2. The heart rate monitor 100 may further include a user interface 102 that may display information, such as heart rate, time, etc., to the user, as well as serve as a touch pad for user input. If desired, the heart rate monitor 100 may include hard buttons (not shown) for user input.

The PPG sensor 110 may be a conventional PPG sensor that illuminates the skin of user 101 and measures changes in the absorption of reflected light to monitor the perfusion of blood to the dermis and subcutaneous tissue of the skin. As the heart pumps blood to the user's wrist, the pressure pulse will distend the arteries and arterioles in the subcutaneous tissue. The change in volume caused by the pressure pulse is detected by the PPG sensor 110 by illuminating the skin with light, e.g., from a light-emitting diode (LED) and measuring the amount of light reflected to a photodiode in the PPG sensor 110.

With the heart rate monitor 100 worn on the wrist of the user 101, however, motion incurred during normal activity or exercise will produce artifacts, referred to herein as noise, in the PPG signal produced by the PPG sensor 110. Moreover, the PPG sensor 110 may be displaced with respect to the user's skin during normal activity or exercise, resulting in additional noise in the PPG signal. Additional sources of noise in the PPG signal may also be present, physiological phenomena that happen inside the body and hardware noise.

The processor 130 receives the PPG signals from the PPG sensor 110 and generates a PPG spectra in discrete windows. A PPG spectrum in a window, however, may include multiple peaks, with one peak corresponding to the user's heart rate, while the remaining peaks correspond to noise in the PPG signal. The peak associated with the user's heart rate will typically be a non-dominant peak and is, therefore, difficult to identify. Accordingly, the processor 130 may use the inertial sensor signals from the inertial sensor 120 to identify and remove noise peaks in the PPG signal. Once the peak corresponding to the user's heart rate is identified, the heart rate is tracked using the identified heart rate as an initial heart rate and adjusting the estimated heart rate based on estimated changes in the heart rate, i.e., whether the heart rate is increasing, decreasing or is constant. Even after removal of noise in the PPG signals, however, the resulting PPG spectrum may still include multiple peaks, only one of which corresponds to the heart rate. If a peak that is associated with noise is incorrectly identified as the initial heart rate, the heart rate will be tracked based on an incorrect initial heart rate, resulting in an inaccurate estimate of the heart rate. Accordingly, the processor 130 includes a reset through which the processor 130 may recognize an error in the selection of the initial heart rate has occurred and may select a new initial value of the user's heart rate.

Figure 3:
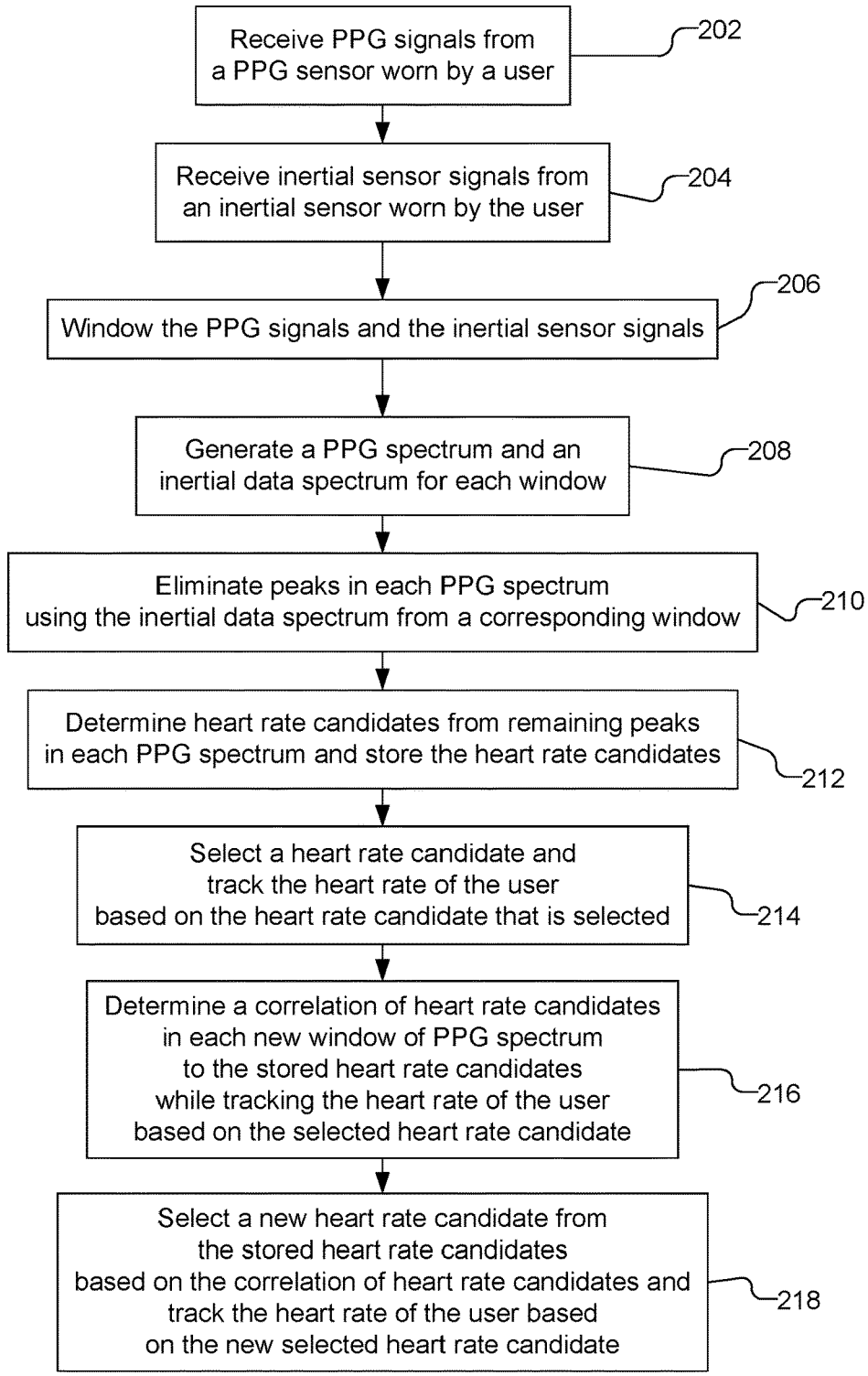
FIG. 3 is a flow chart illustrating a process of resetting the heart rate monitoring in accordance with one implementation.

FIG. 3 is a flow chart illustrating a process of resetting the heart rate monitoring in accordance with one implementation. As illustrated, PPG signals from PPG sensor 110 worn by a user are received (202). Additionally, inertial sensor signals from an inertial sensor 120, which may be accelerometers, worn by the user are received (204). The PPG sensor and inertial sensor are worn on the wrist of the user. The PPG signals and the inertial sensor signals are windowed (206). In other words, a sliding time window of T seconds, e.g., T=2 seconds, is applied to the PPG signals and the inertial sensor signals. The window may slide so that every S seconds, e.g., S≤T, a new window of PPG signals and the inertial sensor signals is produced. A PPG spectrum and inertial data spectrum are generated for each window of the PPG signals and inertial sensor signals (208). The PPG spectrum and inertial data spectrum, for example, may be obtained by converting the time domain representation to a frequency domain representation using a Fast Fourier Transform.

Peaks in each PPG spectrum are eliminated using the inertial data spectrum from a corresponding window (210). For example, peaks in the PGG spectrum that have the same frequency as peaks in the inertial data spectrum may be assumed to be noise caused by movement of the user and therefore may be removed from the PPG spectrum. More than one peak may remain, however. Heart rate candidates are determined from remaining peaks in each PPG spectrum and the heart rate candidates are stored (212). The heart rate candidates may be determined from the remaining peaks in each PPG spectrum by performing blind source separation on the PGG signals in the time domain using the inertial data spectrum and the PPG spectrum to reduce a number of the remaining peaks to produce a subset of the remaining peaks, wherein the subset of the remaining peaks are the heart rate candidates. For example, noise removal may be performed by notching out frequencies that appear in the inertial data spectrum and the PPG signal may be additionally filtered with blind source separation using the inertial data spectrum. Blind source separation is a well-known signal processing technique in which source signals are separated from a set of mixed signals where there is little or no information about the source signals or the mixing process. Examples of blind source separation, any of which may be used herein, include, principal components analysis; independent component analysis; dependent component analysis; non-negative matrix factorization; low-complexity coding and decoding; stationary subspace analysis; and common spatial pattern.

A heart rate candidate is selected and the heart rate of the user is tracked based on the heart rate candidate that is selected (214). For example, the heart rate candidate may be selected as a primary peak within the subset of the remaining peaks. Alternatively, the heart rate candidate may be selected as the only remaining peak in the subset of the remaining peaks.

Referring back to FIG. 3, a correlation is determined for heart rate candidates in each new window of PPG spectrum to the heart rate candidates that are stored while the heart rate of the user is continually tracked based on the heart rate candidate that is selected (216). A new heart rate candidate is selected from the heart rate candidates that are stored based on the correlation of heart rate candidates and the heart rate of the user is tracked based on the new heart rate candidate that is selected (218).

Figure 4:
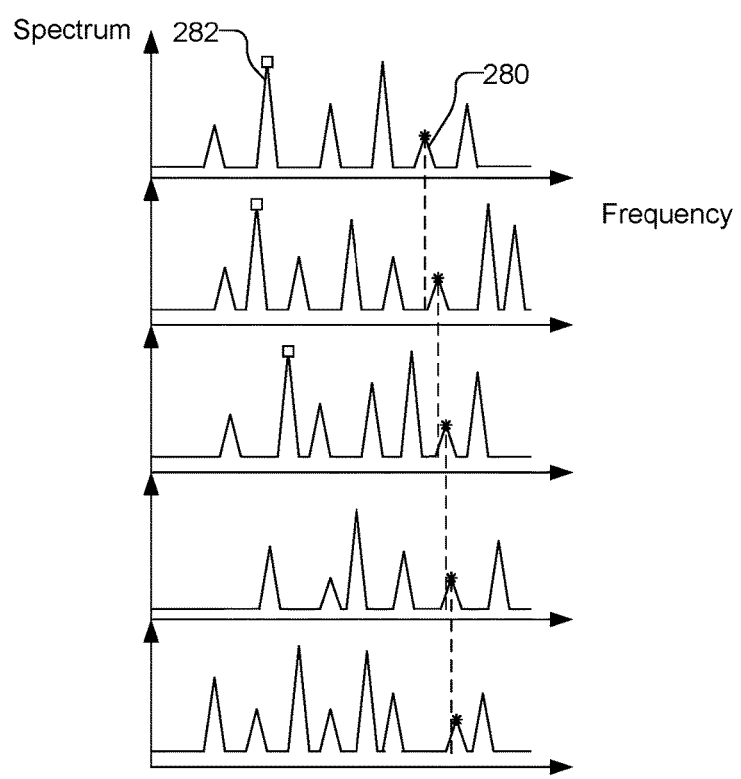
FIG. 4 illustrates a number of PPG spectra over five consecutive windows.

The correlation between heart rate candidates in each new window of PPG spectrum to the stored heart rate candidates may be determined using a frequency tracker for non-stationary harmonic signals. Tracking non-stationary harmonic signals is a known signal processing method typically used in speech analysis, e.g., in pitch detection algorithms. For example, pitch detection is generally discussed in Stephen A. Zahorian and Hongbing Hu, "A Spectral/temporal method for Robust Fundamental Frequency Tracking," The Journal of the Acoustical Society of America, 123 (6), 2008, which is incorporated herein by reference. By way of example, FIG. 4 illustrates a number of PPG spectra over five consecutive windows. Each spectrum includes a plurality of peaks, each of which is a heart rate candidate, and the peak 280 with the star corresponds to the actual heart rate value. Each new spectrum that is generated for a window is correlated to the previous spectra. If the incorrect peak, e.g., peak 282 with the square were selected as the heart rate, tracking would be based on the peak 282. By determining a correlation for heart rate candidates in each new window of PPG spectrum to the previously stored heart rate candidates, while continually tracking the heart rate, the correct heart rate value, e.g., peak 280, may eventually be determined and selected as the new heart rate value to be used to track the heart rate. For example, after several windows, there will be a poor correlation between heart rate candidates that are due to noise. As illustrated in FIG. 4, while the first three windows of spectra include the peak 282, which is due to noise, eventually the peak 282 is no longer present in spectrum. On the other hand, the peak 280 that corresponds to the actual heart rate value is well correlated over multiple windows of spectra. It should be noted that because heart rates change over time, the correlation between heart rate candidates in windows must account for the non-stationary frequency of the heart rate. Thus, the peak 282 may be selected as the new heart rate candidate and the heart rate is tracked based on peak 282. The selection of a new heart rate candidate may occur, e.g., when the determined correlation for the new heart rate candidate is better than the correlation for a previously selected heart rate candidate. For example, a correlated candidate that is relatively close, e.g., within a set threshold, from the previously selected frequency, may be selected as the new heart rate candidate. For example, a reasonable value for such a threshold is the maximum change of a heart rate within the time of a sliding window, e.g., 8 bpm if the window slides every 2 seconds.

Figure 5:
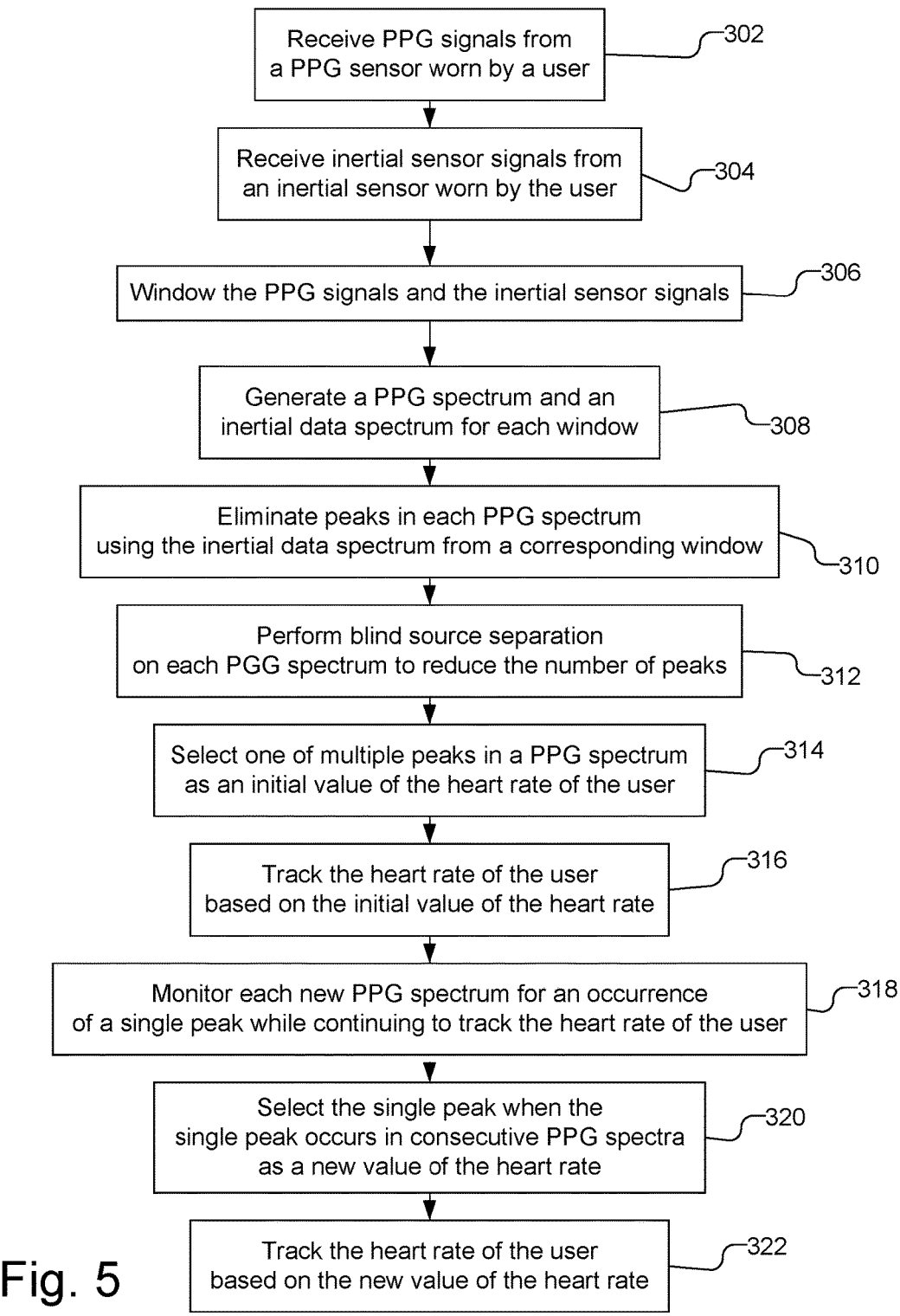
FIG. 5 is a flow chart illustrating a process of resetting the heart rate monitoring in accordance with another implementation.

FIG. 5 is a flow chart illustrating a process of resetting the heart rate monitoring by the processor 130 in accordance with another implementation. The method of FIG. 5 is similar to the method described in FIG. 3 discussed above. As illustrated, PPG signals from PPG sensor 110 worn by a user are received (302). Additionally, inertial sensor signals from an inertial sensor 120, which may be accelerometers, worn by the user are received (304). The PPG sensor and inertial sensor are worn on the wrist of the user. The PPG signals and the inertial sensor signals are windowed (306). In other words, a sliding time window of T seconds is applied to the PPG signals and the inertial sensor signals. A PPG spectrum and inertial data spectrum are generated for each window of the PPG signals and inertial sensor signals (308). The PPG spectrum and inertial data spectrum, for example, may be obtained by converting the time domain representation to a frequency domain representation using a Fast Fourier Transform.

Peaks in each PPG spectrum are eliminated using the inertial data spectrum from a corresponding window (310). For example, peaks in the PGG spectrum that have the same frequency as peaks in the inertial data spectrum may be removed from the PPG spectrum. More than one peak may remain, however. One of multiple peaks in a PPG spectrum is selected as an initial value of the heart rate of the user (314). Additionally, blind source separation may be performed on the PGG signals in a time domain using the inertial data spectrum and the PPG spectrum to further reduce the number of the remaining peaks to produce a subset of the remaining peaks, wherein the initial value of the heart rate is selected from the subset of the remaining peaks (312).

The heart rate of the user is tracked based on the initial value of the heart rate (316). Each new PPG spectrum is monitored for an occurrence of a single peak while continuing to track the heart rate of the user based on the peak that was previously selected (318). The heart rate monitoring may be reset by selecting the single peak when the single peak occurs in consecutive PPG spectra as a new value of the heart rate (320). For example, if the single peak occurs in five consecutive PPG spectra, the single peak may be selected as the new value of the heart rate. The heart rate of the user is tracked based on the new value of the heart rate (322).

Figure 6:
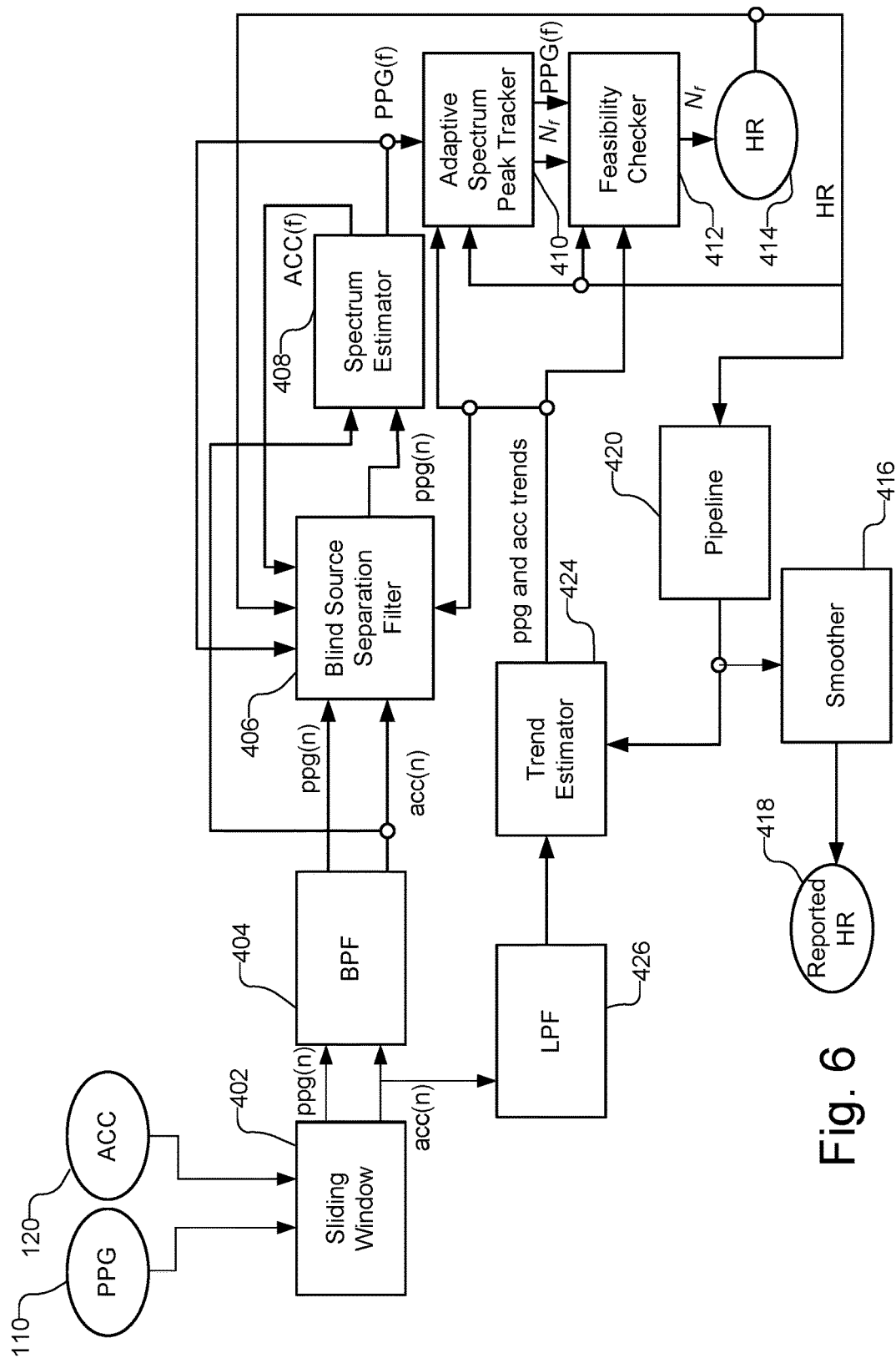
FIG. 6 is an architecture diagram for the heart rate monitor.

FIG. 6 is an architecture diagram for the heart rate monitor 100. As illustrated, the PPG sensor 110 and inertial sensor 120, which may be an accelerometer and is labeled ACC, provide signals to a sliding window 402. The sliding window 402 windows the data from the PPG sensor 110 and inertial sensor 120 so that data is separated into windows of T seconds, e.g., 2 seconds, that increment every S seconds, e.g., 2 seconds. Of course, smaller or larger windows may be used and the windows may overlap if desired, where a large overlap permits reporting heart rates more frequently but requires additional computations, and a small overlap permits less computations but heart rates are reported less frequently. The sliding window 402 produces windowed PPG signals ppg(n) and inertial sensor signals acc(n), which are provided to a band pass filter (BPF) 404. The band pass filter 404 passes only a desired band of the PPG signals and inertial sensor signals to remove noise that is outside the frequency band of interest, e.g., between 0.8 Hz and 3.3 Hz.

After the band pass filter 404, the PPG signals ppg(n) and inertial sensor signals acc(n) are provided to a blind source separation filter 406, which filters out the noise. The blind source separation filter 406 filters out the noise by decomposing the time domain PPG sensor signals ppg(n) into a number of simplified time domain signals. The spectrum for each simplified signal are computed and are used along with an inertial data spectrum ACC(f) produced by spectrum estimator 408, to identify the signals that have noise characteristics. The blind source separation filter 406 reduces the number of the remaining peaks by eliminating those simplified signals that have noise characteristics. The blind source separation filter 406 then uses the remaining simplified signals them to reconstruct the original PPG signal, the spectrum for which will contain a subset of the remaining peaks in the PPG sensor signals. If desired, the blind source separation filter 406 may additionally use the PPG spectrum PPG(f) produced by spectrum estimator 408, the current heart rate HR from heart rate converter 414, and the trends in the PPG signals and the inertial sensor signals (ppg and acc trends) from the trend estimator 424, to identify and remove noise.

Figure 7:
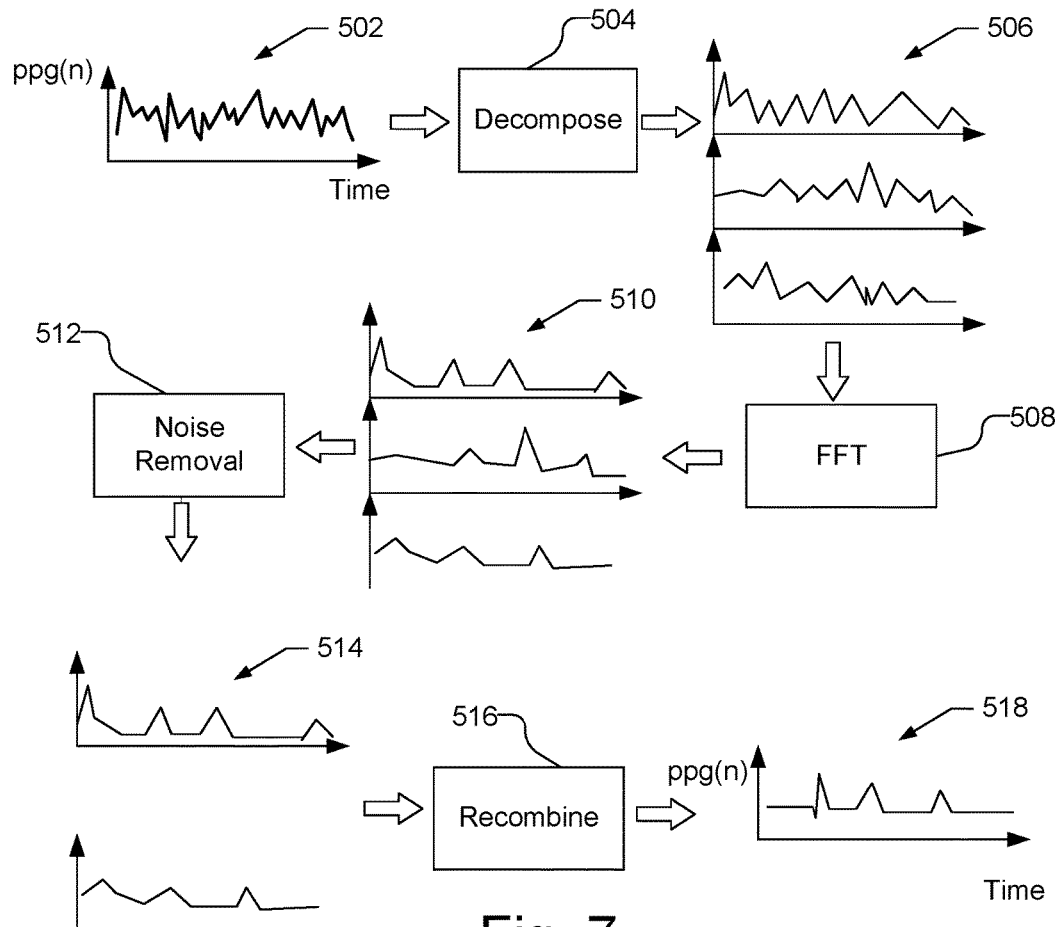
FIG. 7 illustrates the operation of a blind source separation filter in the heart rate monitor.

FIG. 7, by way of example, illustrates the operation of the blind source separation filter 406. As can be seen, the blind source separation filter 404 receives the PPG signal 502 and decomposes 504 the time domain PPG signal into a plurality of more simple decomposed signals 506, e.g., using singular value decomposition or a similar technique, which are converted into spectra 510 in the frequency domain, e.g., using a Fast Fourier Transform 508. Noise characteristics in identified and removed 512 by comparing each spectrum in spectra 510 to the inertial data spectrum ACC(f) produced by spectrum estimator 408 and eliminating any spectrum that has noise characteristics, i.e., have peaks that within a threshold amount from the inertial data spectrum ACC(f), resulting in spectra 514. For example, the threshold may be within 2 frequency bins of the inertial data spectrum ACC(f) peaks. The simple decomposed signals 506 that correspond to the remaining spectra 514 are recombined 516 to reconstruct the PPG signal 518, but with peaks corresponding to noise removed.

The blind source separation filter 406 identifies noise by comparing the inertial data spectrum ACC(f), produced by the spectrum estimator 408, to the decomposed signals and eliminates peaks in the PPG sensor signals that are the same or nearly the same as dominant peaks in the inertial data spectrum ACC(f). If, however, a dominant peak in the inertial sensor spectrum ACC(f) matches the previous heart rate HR, as provided by heart rate converter 414, that peak is not removed from the PPG sensor signals.

If desired, additional noise criteria may be used in the blind source separation filter 406 to identify and remove noise from the PPG sensor signals. For example, the maximum singular value may be observed and used as a threshold to eliminate anything less, e.g., any peaks less than 1% of max value may be removed. For example, the spectrum 510 associated with a simple decomposed signal 506, shown in FIG. 7, may be associated with a singular value. The simple decomposed signals having a spectrum with a small singular value, e.g., less than 1% of the maximum singular value, may be eliminated.

Additionally, if there are more than two dominant peaks in the spectrum 510 of the simple decomposed signals 506, the blind source separation filter 406 may eliminate those signals. Dominant peaks may be determined, e.g., as any peak that is greater than a designated percentage of the maximum peak, e.g., 90%.

Additionally, the blind source separation filter 406 may eliminate peaks in the PPG sensor signals using a threshold that is based on a maximum possible change in a heart rate within specific period of time. For example, in general, it is unlikely that a heart rate will change more than 10 beats/min within a 2 second window. Accordingly, if a peak in the PPG sensor signals represents a frequency (or heart rate) that is more than a threshold amount from the previous heart rate HR, as provided by heart rate converter 414, the peak may be eliminated. Additionally, because the previous heart rate HR may not be correct, the blind source separation filter 406 may compare peaks in the PPG sensor signals to an average heart rate determined based on the previous heart rate HR and the peaks in the PPG spectrum ACC(f) as provided by the spectrum estimator 408, that are closest to the previous heart rate HR. For example, an average heart rate $\overline{N}$ as $$\overline{N} = \frac{N_{prev} + N_{new}}{2} \quad \text{eq. 1}$$

where $N_{prev}$ is the previous heart rate and $N_{new}$ is an average of the closest peaks in the PPG spectrum ACC(f) to the previous heart rate $N_{prev}$, e.g., where peaks are considered close if they are within a threshold amount from the previous heart rate $N_{prev}$.

Additionally, the blind source separation filter 406 may eliminate peaks in the PPG sensor signals if the peaks are not consistent with the ppg trend as provided by the trend estimator 424. In other words, if the trend estimator 424 estimates that the heart rate is increasing, then the blind source separation filter 406 may eliminate any peaks in the PPG sensor signals that are less than a threshold from the previous heart rate HR, e.g., 3 bpm or less than the previous estimated heart rate HR. Similarly, if the trend estimator 424 estimates that the heart rate is decreasing, then the blind source separation filter 406 may eliminate any peaks in the PPG sensor signals that are more than a threshold from the previous heart rate HR.

Additional, fewer or different criteria for identifying and removing noise from the PPG sensor signals may be used by the blind source separation filter 406 if desired. After the noise is identified and removed from the decomposed signals, the decomposed signals are recombined to produce the PPG sensor single ppg(n) with peaks corresponding to noise removed.

The resulting PPG sensor single ppg(n) is received by the spectrum estimator 408, which also receives the inertial sensor signal acc(n). The spectrum estimator 408 converts the PPG sensor single ppg(n) and the inertial sensor signal acc(n) in each window into the frequency domain PPG spectrum PPG(f) and inertial data spectrum ACC(f), respectively, e.g., using a Fast Fourier Transform. The remaining peaks in the resulting PPG spectrum PPG(f) in each window are the heart rate candidates and are provided to the adaptive spectrum peak tracker 410. The resulting PPG spectrum PPG(f) may also be provided to the blind source separation filter 406 along with the resulting inertial data spectrum ACC(f).

The adaptive spectrum peak tracker 410 receives the PPG spectrum PPG(f) from the spectrum estimator 408, as well as the current heart rate HR from heart rate converter 414, and the trends in the PPG signals and the inertial sensor signals (ppg and acc trends) from the trend estimator 424. The PPG spectrum PPG(f) in each window may include more than one peak, i.e., there may be multiple heart rate candidates. The adaptive spectrum peak tracker 410 may select one of the peaks as corresponding to the heart rate, and thus, is the frequency of the heart rate $N_f$. The adaptive spectrum peak tracker 410 may select a peak from the PPG spectrum PPG(f), e.g., by comparing peaks from the inertial data spectrum ACC(f) and the PPG spectrum PPG(f) over multiple windows, and determining which peak in the PPG spectrum PPG(f) corresponds to the heart rate peak and which peaks correspond to noise. Additionally, the adaptive spectrum peak tracker 410 may eliminate heart rate candidates that are not consistent with the heart rate trend as provided by the trend estimator 424. In other words, if the trend estimator 424 estimates that the heart rate is increasing, then the adaptive spectrum peak tracker 410 may eliminate any heart rate candidates that are less than a threshold from the previous heart rate HR, e.g., 3 bpm or less than the previous estimated heart rate HR. Similarly, if the trend estimator 424 estimates that the heart rate is decreasing, then the adaptive spectrum peak tracker 410 may eliminate any heart rate candidates that are more than a threshold from the previous heart rate HR.

The selected value of the heart rate $N_f$ may be used to track the heart rate of the user. However, the adaptive spectrum peak tracker 410 may reset the value of the heart rate $N_f$ if it determines that the previously selected value is incorrect. For example, as discussed in reference to FIG. 5, each new PPG spectrum PPG(f) is monitored for an occurrence of a single peak, while the heart rate of the user is continually tracked based on a previously selected value of the heart rate $N_f$. If a single peak occurs over a number of consecutive windows, e.g., five consecutive windows, the heart rate may be reset by selecting the single peak as the new value of the heart rate.

The selected value of the heart rate $N_f$ is provided to a feasibility checker 412, which also receives the current heart rate HR from heart rate converter 414, and the trends in the PPG signals and the inertial sensor signals (ppg and acc trends) from the trend estimator 424. The feasibility checker 412 determines whether the selected value of the heart rate $N_f$ is feasible and may reset the value for the heart rate $N_f$ if it determines that the selected value of the heart rate $N_f$ is incorrect. For example, as discussed in reference to FIG. 3, the heart rate of the user may be continually tracked while the feasibility checker 412 may determine a correlation for heart rate candidates, i.e., peaks, in each new window of spectrum PPG(f) to the heart rate candidates from previous windows. If a non-selected heart rate candidate is determined to have a better correlation with heart rate candidates from previous windows, the feasibility checker 412 may switch the value of the heart rate $N_f$ to the heart rate candidate with the better correlation.

The selected value of the heart rate $N_f$ is provided to the heart rate converter 414. The heart rate converter 414 converts the final selected frequency of the heart rate $N_f$ to a heart rate HR by scaling it. The current value of the heart rate HR is provided to the blind source separation filter 406, the adaptive spectrum peak tracker 410, the feasibility checker 412, as well as the pipeline 420.

The smoother 416 receives the heart rate HR from the pipeline 420 and smoothes the heart rate HR, e.g., using a low pass filter or a median filter on the last K reported HR values, e.g., K may be 10. The smoother 416 provides the reported heart rate 418, which may be displayed to the user, or provided to other applications on the heart rate monitor 100 or a remote device, e.g., using wireless communications, such as Blue Tooth or the like.

The heart rate HR is further provided from the pipeline 420 to the trend estimator 424. The trend estimator 424 additionally receives the inertial sensor signals acc(n) after passing through a low pass filter 426. The low pass filter 426 keeps only low frequency components in the inertial sensor signals acc(n), e.g., less than 0.2 Hz. The trend estimator 424 uses the inertial sensor signals and the previous history of the heart rate HR to determines the trends in the inertial sensor data and the heart rate, e.g., whether user movement is increasing, decreasing or staying the same and whether the user heart rate is increasing, decreasing or staying the same. The trend may be found, e.g., by determining the slope of the last M values of the heart rate HR or inertial sensor signals, wherein if the slope is positive, the trend is upward, if the slope is negative, the trend is downward, and if the slope is zero, the trend is flat. The trends in the PPG signals, i.e., heart rate, and the inertial sensor signals (ppg and acc trends) is provided to the blind source separation filter 406, the adaptive spectrum peak tracker 410 and the feasibility checker 412, as discussed above.

Figure 8:
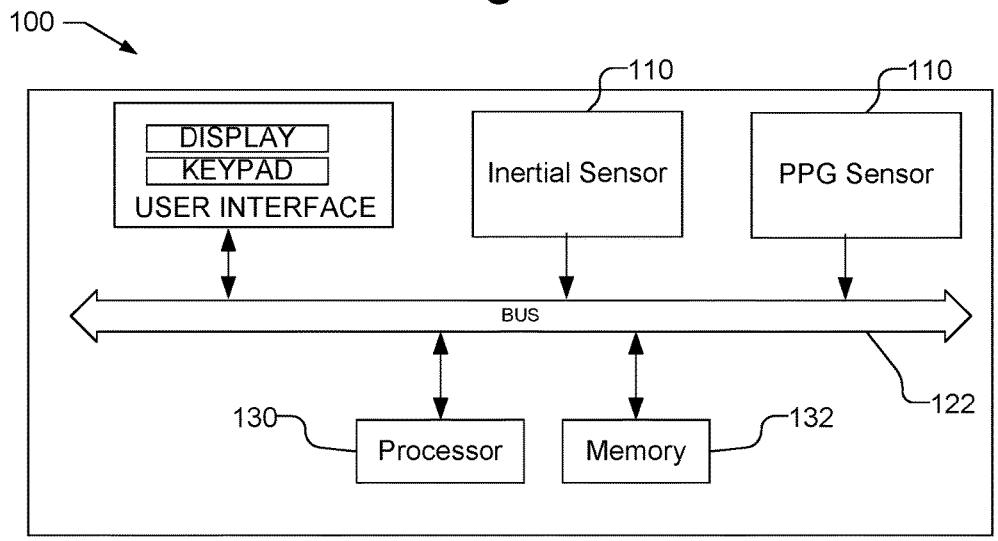
FIG. 8 is a block diagram of the heart rate monitor.

FIG. 8 is a block diagram of the heart rate monitor 100, which is wrist worn by the user and includes a PPG sensor 110, multiple axis inertial sensor 120, and processor 130 as discussed herein. The PPG sensor 110 may be an optical PPG sensor. The multiple axis inertial sensor 120 may include two or three axes and may be, for example, a three axis accelerometer, gyroscopes, or the like. The heart rate monitor 100 further includes a user interface 102 that may include, e.g., a display, as well as a real or virtual keys or other input device through which the user may, e.g., input information, make selections.

As illustrated, the PPG sensor 110, inertial sensor 120, and user interface 102 are coupled to the processor 130, e.g., a bus 122. Thus, the processor 130 is connected to receive signals from the PPG sensor 110 and the inertial sensor 110 and to communicate with the user interface 102. The processor 130 is further connected to memory 132, e.g., via the bus 122. The processor 130 is configured to receive and processes the signals from the PPG sensor 110 and inertial sensor 120 as described herein. For example, the architecture discussed in FIG. 6 may be implemented within processor 130. It should be understood, however, that the particular architecture used in the heart rate monitor 100 may vary if desired. The methodologies described herein may be implemented by various means depending upon the application. For example, the processor 130 may implement the methodologies discussed herein using hardware, firmware or software. For example, the architecture discussed in FIG. 6 may be implemented in the processor 130 based on instructions in software or firmware which may be stored in memory 132 and run in the processor 130. Further, it should be understood that the processor 130 may be one or more processors operating together to perform the functions discussed herein.

For example, the processor 130 may, but need not necessarily include, one or more microprocessors, embedded processors, controllers, application specific integrated circuits (ASICs), digital signal processing devices (DSPDs), programmable logic devices (PLDs), field programmable gate arrays (FPGAs), and the like. Moreover, as used herein the term "memory" refers to any type of computer storage medium, including long term, short term, or other memory associated with the mobile device, and is not to be limited to any particular type of memory or number of memories, or type of media upon which memory is stored.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in memory 132 and executed by the processor 130. Memory 132m may be implemented within or external to the processor 130. If implemented in firmware and/or software, the functions may be stored as one or more instructions or code on a computer-readable medium. Examples include non-transitory computer-readable media encoded with a data structure and computer-readable media encoded with a computer program. Computer-readable media includes physical, i.e., non-transitory, computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method for monitoring a heart rate, the method comprising:
    receiving photoplethysmogram (PPG) signals from a PPG sensor worn by a user;
    receiving inertial sensor signals from an inertial sensor worn by the user;
    windowing the PPG signals and the inertial sensor signals;
    generating a PPG spectrum and an inertial data spectrum for each window of the PPG signals and the inertial sensor signals;
    eliminating peaks in each PPG spectrum using the inertial data spectrum from a corresponding window;
    determining a plurality of heart rate candidates from remaining peaks in each PPG spectrum and storing the plurality of heart rate candidates;
    selecting a heart rate candidate and tracking the heart rate of the user based on the heart rate candidate that is selected;
    reporting the tracked heart rate of the user that is based on the heart rate candidate that is selected;
    determining a correlation of heart rate candidates in each new window of PPG spectrum to the plurality of heart rate candidates that are stored while continuing to track the heart rate of the user based on the heart rate candidate that is selected;
    selecting a new heart rate candidate from the plurality of heart rate candidates that are stored based on the correlation of heart rate candidates and tracking the heart rate of the user based on the new heart rate candidate that is selected; and
    reporting the heart rate of the user that is based on the new heart rate candidate that is selected.

2. The method of claim 1, wherein generating the PPG spectrum and the inertial data spectrum comprises converting a time domain representation of PPG signals for each window into a frequency domain representation using a Fast Fourier Transform and converting a time domain representation of inertial sensor signals for each window into a frequency domain representation using the Fast Fourier Transform.

3. The method of claim 1, wherein the PPG sensor and the inertial sensor are worn on a wrist of the user.

4. The method of claim 1, wherein the inertial sensor comprises accelerometers.

5. The method of claim 1, wherein determining the plurality of heart rate candidates from the remaining peaks in each PPG spectrum comprises performing blind source separation on the PPG signals in a time domain using the inertial data spectrum and the PPG spectrum to reduce a number of the remaining peaks to produce a subset of the remaining peaks, wherein the subset of the remaining peaks are the plurality of heart rate candidates.

6. The method of claim 5, wherein selecting the heart rate candidate comprises selecting a primary peak or an only remaining peak from the subset of the remaining peaks.

7. The method of claim 1, further comprising determining a heart rate trend and a physical activity trend rate and using them to determine if the heart rate is correct.

8. The method of claim 1, wherein reporting the tracked heart rate of the user comprises at least one of displaying the tracked heart rate to the user, providing the tracked heart rate to an application; wirelessly providing the tracked heart rate to a remote device.

9. A heart rate monitor that is worn by a user and monitors a heart rate of the user, the heart rate monitor comprising:
a photoplethysmogram (PPG) sensor that monitors the user and produces PPG signals;
an inertial sensor that produces inertial sensor signals in response to user motion;
a display for displaying a heart rate of the user;
a processor coupled to receive the PPG signals from the PPG sensor and the inertial sensor signals from the inertial sensor and coupled to the display, the processor being configured to window the PPG signals and the inertial sensor signals, generate a PPG spectrum and an inertial data spectrum for each window of the PPG signals and the inertial sensor signals, eliminate peaks in each PPG spectrum using the inertial data spectrum from a corresponding window, determine a plurality of heart rate candidates from remaining peaks in each PPG spectrum and store the plurality of heart rate candidates, select a heart rate candidate and tracking the heart rate of the user based on the heart rate candidate that is selected, cause the display to display the tracked heart rate of the user that is based on the heart rate candidate that is selected, determine a correlation of heart rate candidates in each new window of PPG spectrum to the plurality of heart rate candidates that are stored while continuing to track the heart rate of the user based on the heart rate candidate that is selected, select a new heart rate candidate from the plurality of heart rate candidates that are stored based on the correlation of heart rate candidates and tracking the heart rate of the user based on the new heart rate candidate that is selected; and cause the display to display the heart rate of the user that is based on the new heart rate candidate that is selected.

10. The heart rate monitor of claim 9, wherein the processor is configured to generate the PPG spectrum and the inertial data spectrum by being configured to convert a time domain representation of PPG signals for each window into a frequency domain representation using a Fast Fourier Transform and convert a time domain representation of inertial sensor signals for each window into a frequency domain representation using the Fast Fourier Transform.

11. The heart rate monitor of claim 9, wherein the PPG sensor and the inertial sensor are configured to be worn on a wrist of the user.

12. The heart rate monitor of claim 9, wherein the inertial sensor comprises accelerometers.

13. The heart rate monitor of claim 9, wherein the processor is configured to determine the plurality of heart rate candidates from the remaining peaks in each PPG spectrum by being configured to perform blind source separation on the PPG signals in a time domain using the inertial data spectrum and the PPG spectrum to reduce a number of the remaining peaks to produce a subset of the remaining peaks, wherein the subset of the remaining peaks are the plurality of heart rate candidates.

14. The heart rate monitor of claim 13, wherein the processor is configured to select the heart rate candidate by being configured to select a primary peak or an only remaining peak from the subset of the remaining peaks.

15. The heart rate monitor of claim 9, wherein the processor is further configured to determine a heart rate trend and a physical activity trend rate and using them to determine if the heart rate is correct.

16. The heart rate monitor of claim 9, wherein the processor is further configured to provide the tracked heart rate to an application or wirelessly provide the tracked heart rate to a remote device.

* * * * *